United States Patent
Fischer et al.

(10) Patent No.: US 12,414,833 B2
(45) Date of Patent: Sep. 16, 2025

(54) TEST DEVICE

(71) Applicant: Erbe Elektromedizin GmbH, Tuebingen (DE)

(72) Inventors: Klaus Fischer, Nagold (DE); Alexander Neugebauer, Moessingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 1010 days.

(21) Appl. No.: 17/499,031

(22) Filed: Oct. 12, 2021

(65) Prior Publication Data

US 2022/0117690 A1    Apr. 21, 2022

(30) Foreign Application Priority Data

Oct. 19, 2020   (DE) ............... 10 2020 127 424.6

(51) Int. Cl.
*A61B 18/14*    (2006.01)
*A61B 90/00*    (2016.01)

(52) U.S. Cl.
CPC ............ *A61B 90/08* (2016.02); *A61B 18/14* (2013.01); *A61B 2560/0223* (2013.01)

(58) Field of Classification Search
CPC .......... A61B 18/1206; A61B 18/14; A61B 2018/00904; A61B 2562/00; A61B 2218/005; A61B 2560/0223; A61B 90/08
See application file for complete search history.

(56) References Cited

U.S. PATENT DOCUMENTS

| | | |
|---|---|---|
| 6,157,041 A | 12/2000 | Thomas et al. |
| 8,157,795 B2 * | 4/2012 | Sartor ............... A61B 18/042 606/41 |
| 9,486,128 B1 * | 11/2016 | Hannaford ........... A61B 18/20 |
| 9,851,396 B2 * | 12/2017 | Nold ................. A61B 18/18 |
| 10,154,786 B2 | 12/2018 | Fischer et al. |
| 10,251,695 B2 | 4/2019 | Fischer et al. |
| 2003/0023170 A1 | 1/2003 | Gardner et al. |
| 2004/0033618 A1 | 2/2004 | Haass et al. |
| 2005/0014997 A1 | 1/2005 | Ruchti et al. |
| 2009/0088772 A1 | 4/2009 | Blumenkranz |
| 2010/0019125 A1 | 1/2010 | Stefani et al. |
| 2014/0378961 A1 | 12/2014 | Fischer et al. |
| 2016/0000330 A1 | 1/2016 | Huang et al. |

(Continued)

FOREIGN PATENT DOCUMENTS

| | | |
|---|---|---|
| CN | 101137322 A | 3/2008 |
| CN | 101229419 A | 7/2008 |
| CN | 101511261 A | 8/2009 |

(Continued)

OTHER PUBLICATIONS

D. Spether et al., "Real-Time Tissue Differentiation Based on Optical Emission Spectroscopy for Guided Electrosurgical Tumor Resection." Biomedical Optics Express, vol. 6, No. 4, Apr. 1, 2015.

*Primary Examiner* — Michael F Peffley
(74) *Attorney, Agent, or Firm* — Blank Rome LLP

(57) ABSTRACT

A test device and method for testing and/or calibrating an analysis device for analyzing light appearances created by an RF surgical instrument. The test device has a test object configured for creation of a plasma test light appearance, the light of which can be received by a light receiving unit.

20 Claims, 7 Drawing Sheets

(56) References Cited

U.S. PATENT DOCUMENTS

2019/0254737 A1    8/2019   Fischer et al.
2020/0237421 A1    7/2020   Ataman et al.

FOREIGN PATENT DOCUMENTS

| DE | 10249674 A1 | 5/2004 |
|----|-------------|--------|
| EP | 1693014 A1 | 8/2006 |
| EP | 2 659 846 A1 | 11/2013 |
| EP | 2 815 695 A1 | 12/2014 |
| EP | 2 815 713 A1 | 12/2014 |
| EP | 1737402 B1 | 5/2016 |
| WO | 2007083991 A1 | 7/2007 |
| WO | 2013164109 A1 | 11/2013 |

\* cited by examiner

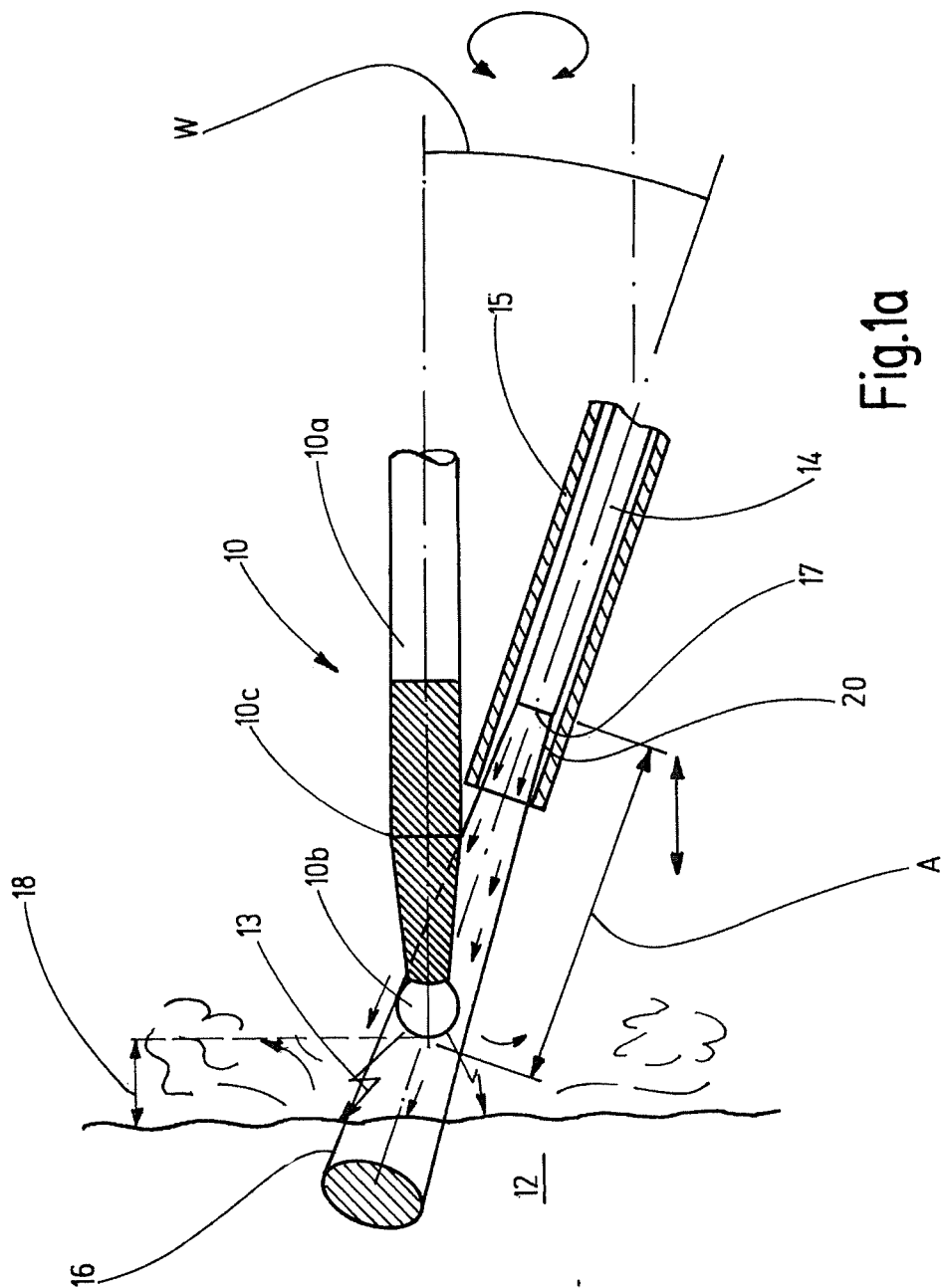
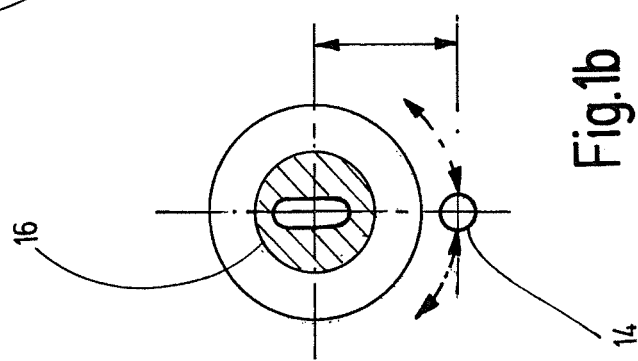
Fig.1a
Fig.1b

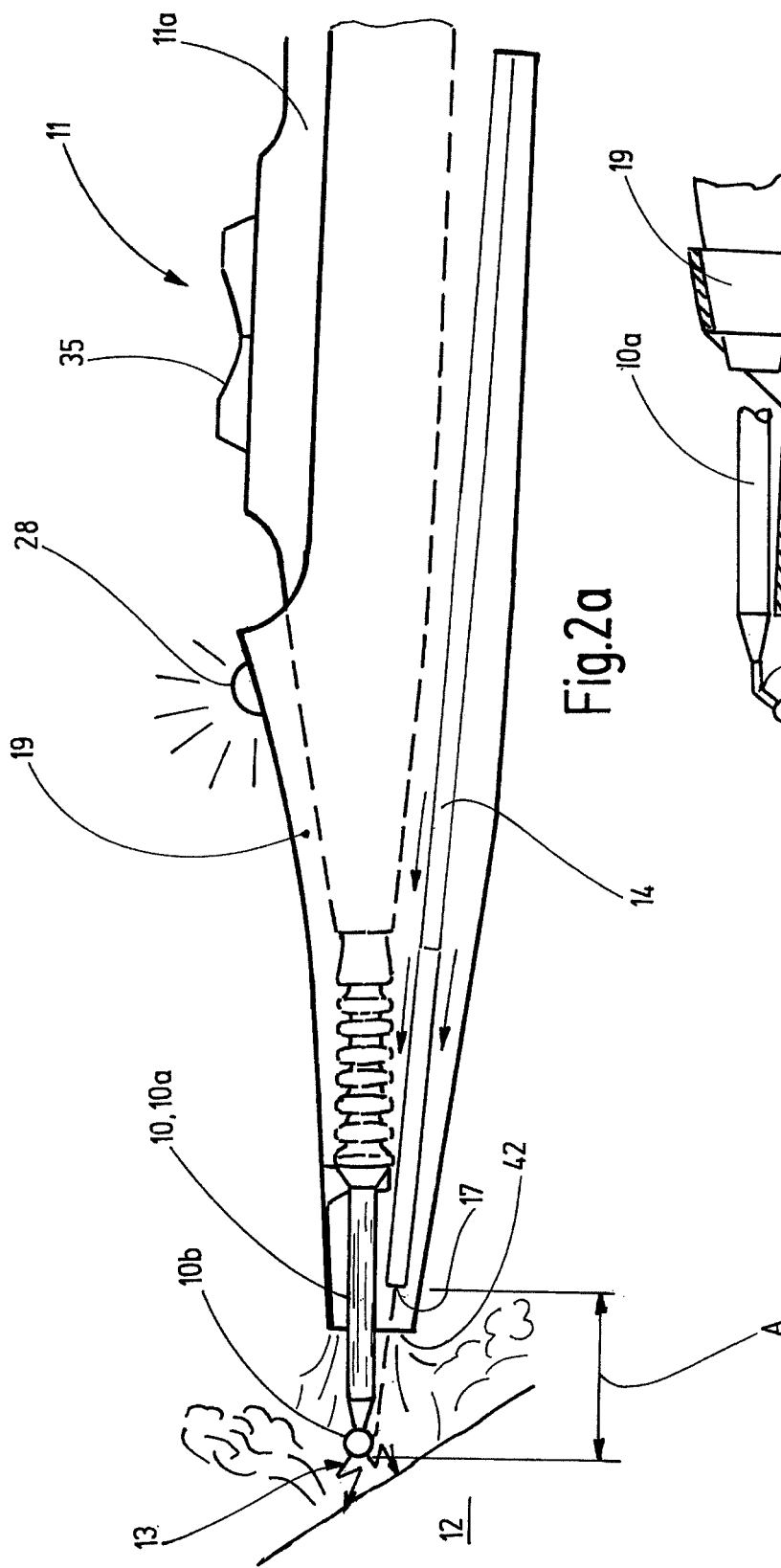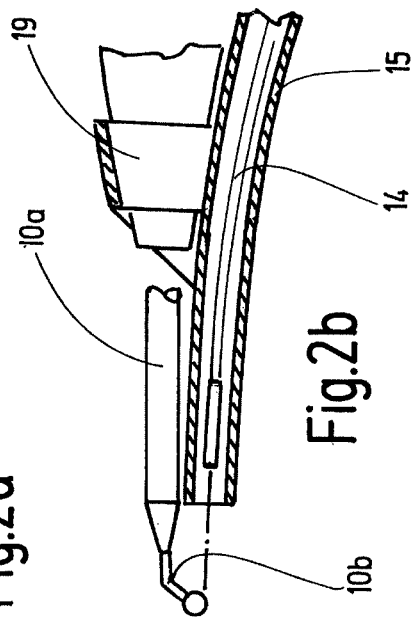

TEST DEVICE

CROSS-REFERENCE TO RELATED APPLICATION

This application claims priority to German Application No. 10 2020 127 424.6, filed Oct. 19, 2020, the entirety of which is incorporated by reference herein.

TECHNICAL FIELD

Embodiments of the invention relate to the field of analysis of light appearances created by electrosurgical intervention on tissue.

BACKGROUND

In the article published in the specialized journal BIO-MEDICAL OPTICS EXPRESS of the authors Spether et al. "Real-time tissue differentiation based on optical emission spectroscopy for guided electrosurgical tumor resection" a pre-clinical study is described in the context of which a light appearance has been created between a tissue sample and an instrument and subsequently evaluated, wherein the tissue sample has been extracted from a patient's organ by surgery.

A surgical device having an instrument for intervention on biological tissue under creation of a light appearance is known from EP 2 659 846 A1. The device comprises an analysis device for determination of light features of the light created by electrical intervention on the tissue and a discriminator device for assignment of light features of the light created during the intervention to tissue features of biological tissue subject to the intervention. EP 2 659 846 A1 proposes to store reference spectra or characteristic light features of healthy and diseased tissue, different tissue types, etc. in a database. The database can be static, i.e. filled with respective data prior to start of surgery. It could also be possible to gain data prior to or during the surgery or to adjust data subsequently. For example, it can be provided that the surgeon stores at least one occurring light feature as desired parameter as long as he securely cuts inside a specific tissue (e.g. healthy tissue). Determined deviations of this desired parameter recognized at a later point of time can be detected by the discriminator device in order to create a signal. The device can further process and transmit this signal. In general it can be said that the discriminator device compares preset or patient individual gained reference spectra or individual light features of these spectra with the measured spectrum or individual light features thereof and creates signals based on deviations that indicate a change of the tissue type or character. Patient individual light features, e.g. a patient individual reference spectrum, can be recorded and stored at the start of a surgery or also one time or multiple times during the surgery.

US 2009/0088772 A1 discloses a surgical instrument carried by a robot that can comprise one or more optical fibers. The optical fiber can be used to transmit and receive photons and can be configured to supply the exciting light as well as transmit scattered photons to an analysis unit, e.g. a spectrophotometer. By means of the optical fiber an optical emission spectroscopy can be carried out in order to detect specific chemical species. The analysis unit can be coupled with a computer in order to provide parameters for calibration of the spectroscopic function of the instrument or for testing the diagnosis. A calibration of the spectrophotometer can be carried out by using of a standard, e.g. standard signals of known solutions or of the tissue chemical composition.

An instrument for electrosurgical intervention on biological tissue is known from EP 2 815 713 A1. It comprises an electrode as well as a light conductor that is connected with a light inlet window formed by a fluid body. The light conductor is connected with a light analysis device in order to capture light created during the RF surgery at the electrode and to supply it to the light analysis device.

SUMMARY

Light receiving units, such as optical fibers, for example, can contaminate during operation, particularly by liquids, precipitation of fumes, steam and particles. In addition, potentially a system consisting of an analysis device having a light receiving unit and an analysis unit as well as an instrument with a specific electrode and an RF generator are in fact first used during a specific surgery.

In an RF generator (energy source for the RF spark) the standard allows, e.g. a standard deviation of the RF output power of +/−20%. The specific electrical resistance of biological tissue varies remarkably, fat tissue has $3.3 \times 10^7$ Ohm mm$^2$/m, muscle tissue $2.0 \times 10^6$ Ohm mm$^2$/m, and blood only $1.6 \times 10^6$ Ohm mm$^2$/m on the contrary. The configurations of different cut or coagulation modes, such as for example, during a spark feedback control, influence the light emission of the RF spark on biological tissue. The specific light emission also depends on the adjustments of the RF generator or the instrument and in addition from the electrode shape.

The configuration of the optical path of the RF-OES-System from the creation up to the analysis unit is a remarkable influencing parameter on the signal quality of light. The optical interfaces at the plug couplings external and internal of the analysis device can remarkably deteriorate the transmission. A contamination of the optical fiber, e.g. during manufacturing process, may deteriorate or even completely impede transmission. An erroneous mechanical attachment of the optical fibers can remarkably deteriorate transmission. Errors during the connection of an analysis device with a surgical instrument and/or during alignment with regard to one another can result in that no usable light signal can be received by the analysis device. Also during the clinical use of an RF-OES-System (Radio Frequency Optical Emission Spectroscopy System) the signal quality of an RF spark can change remarkably, e.g. due to contamination of the optical fiber by blood and can thus distort a tissue distinction or make it impossible.

Due to the energy input, a large variance of intensities can result, particularly RF sparks of different intensity, during the optical emission spectroscopy by using the RF sparks for tissue distinction. The high temperature at the beginning of a spark discharge leads to a pressure increase that in turn enlarges the cross-section of a discharge channel in an explosion-like manner. Thereby the peak temperature is reduced. Temperature and pressure in the plasma are not constant during spark excitation. The impedance of plasma between electrode and tissue varies. In order to be able to compare the RF-OES-Spectra with one another, the RF-OES-Spectra have to comply with a quality criteria respectively in order to sort the tissue in valuable and non-valuable spectra. No absolute values of the signal quality, but only ratios of the single spectral lines relative to one another are determined. The RF spark is not only created between the electrode tip and the tissue, but sparks can also be created laterally outside of the viewing window of the optical fiber due to contamination such that, for example, only a minor part of the light emission is coupled into the glass fiber as compared to a condition without contamination.

Tests or calibrations of single components of a system are potentially of limited meaning only due to the variety of combination possibilities of electrode, light conductor, analysis device, RF generator, adjustment parameters etc.

It is the object of embodiments of the present invention to provide an improved concept for a system having an analysis device for analysis of light appearances created by an RF surgical instrument.

This object is solved by means of a test device for testing, particularly calibrating, an analysis device for analysis of light appearances—created by an RF surgical instrument—according to claim 1. A test object is part of the test device. The test object is configured to create a plasma test light appearance, the light of which can be received by a light receiving unit. The test device is configured for testing, particularly calibrating, at least parts of the analysis device or the entire analysis device. The analysis device can comprise a light receiving unit, e.g. an optical fiber, and an analysis unit, wherein the light receiving unit is connected with the analysis unit. The analysis device serves particularly for tissue distinction (tissue differentiation), e.g. between healthy and malign tissue.

The test object of the test device provides an exogenous test surface (with reference of any human or animal body of a being, particularly the body of the patient that shall be treated with the instrument) such that the test method by means of the test device is not carried out on the human or animal being.

The test object consists preferably of non-biological material. Particularly the test object does not contain human or animal tissue or no human or animal tissue is provided as test object or part of the test object. This however does not exclude that the test object while testing during surgery can be contaminated with tissue residuals or the like.

A plasma test light appearance (briefly test light appearance), as created by means of the test object, means a spark or a continuous plasma, for example. The light appearance can contain electromagnetic waves in the infrared, visible and/or ultraviolet range of the electromagnetic spectrum. The test device can be configured to receive and analyze infrared, visible and/or ultraviolet components of the spectrum of the test light appearance. The light receiving unit that receives the plasma test light appearance can be a test light receiving unit that is connected with the analysis unit of the analysis device or can be connected therewith for test purposes. Preferably, however, the light receiving unit is the light receiving unit of the analysis device. Because the analysis device in combination with the instrument and particularly preferably the RF surgical apparatus for supply of the instrument with RF energy is tested by means of the test device that are also used during specific surgery in preparation to which or during which the analysis device is tested, e.g. calibrated.

A medically educated member of the surgery team, e.g. a surgery assistant or a surgeon can make sure of a principle operability of the analysis device by means of the test device, preferably prior to or during the surgery, in that he/she creates a test light appearance by means of the test object and captures the light by means of the light receiving unit. The test device is preferably configured to output a test result of the operational test, e.g. "test successful", i.e. the analysis device is operable, or "test not successful", i.e. the analysis device is non-operable, by means of a respective signal or by absence of a signal, particularly an optically, acoustically or haptically perceivable signal to the surgery personnel. In doing so, cases can be discovered, for example, in which an optical fiber of the analysis unit is contaminated or defective or in which the analysis unit is not correctly assembled.

Further exemplary advantageous features and embodiments of the inventive test device, the inventive method and the inventive system are derived from the following description.

The test object can comprise a test surface for creation of the test light appearance between an electrode, preferably an electrode of the instrument, and the test surface. The test surface can be formed by a counter electrode to the electrode. The test surface can be electrically conductively connected with the RF surgical apparatus and/or a neutral electrode, in case of a monopolar instrument.

The test device is preferably configured for clinical use. The test device is preferably configured for use during the intraoperative phase of the surgery with the surgical instrument. The test object can be or is arranged in a sterile surgery area. In doing so, the test, particularly calibration, of the analysis device by means of the test device directly before or during the surgery is possible in a particularly simple manner.

Preferably the test device comprises an evaluation unit that is configured to evaluate whether the analysis device is operable based on light features (one light feature or multiple light features) of the captured light of a test light appearance created by means of the test object. The evaluation unit can be part of the analysis device, for example.

Light features for evaluation whether the analysis unit is operable can be, for example: luminous power that is not spectrally distinguished or that is integrated over all captured wavelengths, luminous power at one single wavelength or multiple wavelengths that can be distinguished (distance is larger than the wavelength resolution of the test device), intensities of individual spectral lines, intensities of spectral line groups, time-dependent progress of the test light appearance, polarization of the light of the test light appearance, typical spectra, sections of spectra, signatures gained from spectra and/or signatures gained from the spectra of light of the test light appearance, parts of the spectrum and/or spectral lines. Signatures can be gained as operands from algorithms, formulas, allocation tables or other processing rules. Particularly signatures can be: intensity ratios of selected spectral lines, ratios, sums and/or differences between different terms, wherein the terms can be in turn: sums, differences, products, integrals over spectral parts and/or other terms of intensities of different spectral lines or spectral parts or light features or signatures derived therefrom.

Evaluation criteria can be, for example, signal-to-noise ratio or signal-to-background ratio at a wavelength, groups of wavelengths, sections of the spectrum, the entire spectrum, ratios of intensities at different wavelengths and/or wavelength groups and/or sections of the spectrum. In a simple case, for example, it can be determined by means of the intensity of light of the test light appearance determined by means of the test device by comparison with a threshold whether sufficient light can be captured via the light receiving unit, such that the analysis device is operable.

Alternatively or additionally, a signature of intensity ratios of selected spectral lines of the light of the test light appearance can be calculated and/or the uncertainty of the calculation of the signature, e.g. due to noise or background, can be determined. For example, each signature can be calculated from intensity ratios of selected spectral lines characterizing parts of the material of the test surface and/or electrode and/or atmosphere between electrode and test surface transitioned into plasma condition. If the uncertainty, e.g. the ratio of signature to uncertainty, is greater than a threshold, a positive test of the analysis device can be presumed, for example, wherein the evaluation unit generates a respective evaluation signal. In case of a negative test result, the evaluation unit can create a respective different evaluation signal or no evaluation signal or—as an alternative—the evaluation signal output fails to appear in case of a positive test result. Based on the evaluation signal or the other evaluation signal a particularly acoustically, optically or haptically perceivable signal can be output to the user of the surgical instrument and/or the analysis device and/or the evaluation signal can be used for control of the analysis device test system, the analysis device, the RF surgical instrument and/or the RF surgical apparatus. Based on the evaluation signal, parameter or parameter ranges of the test device, the analysis device, the RF surgical instrument and/or the RF surgical apparatus can be defined, e.g. automatically, by the system. This means that the RF surgical system comprising the RF surgical apparatus, the RF surgical instrument, the test device, the analysis device and/or where appropriate additional devices can be automatically adjusted based on the test of the test device (with or without the allowance of the automatic adjustment by the user), in that at least one adjustment of at least one device of the RF surgical system is selected or modified based on the test. The test device can alternatively or additionally output a recommendation for at least one adjustment of at least one device of the RF surgical system to the user that can then decide to adjust the RF surgical system according to the recommendation.

Due to the evaluation signal, it can be avoided, for example, that the analysis device outputs a signal and/or an indication with regard to the accuracy of the analysis of the analysis device can be derived and output to the user, for example. The evaluation result can thus also be, for example, whether the analysis device operates at all, operates with sufficient accuracy and/or with which accuracy the analysis device is able to operate.

The test device is preferably configured to determine and preferably evaluate a sensitivity of the analysis device at at least one wavelength, a group of wavelengths, in a spectrum part or the entire spectrum and/or a transmissivity of the analysis device at at least one wavelength, a group of wavelengths, a spectrum part or the entire spectrum. The sensitivity is the amount of the electrical signal in the analysis device created by the captured light of the test light appearance in relation to the intensity of the light of the test light appearance. The transmissivity is the ratio of the intensity at the light outlet of the light receiving unit (e.g. an optical fiber) to the intensity at the light inlet of the light receiving unit. For example, the transmissivity can be affected by contamination of the inlet, by damage, e.g. rupture between the light inlet and the light outlet (where the light signal is transferred into an electrical signal) inclusively and/or by coupling pieces between the light inlet and the outlet, for example. Comparison sensitivities and/or transmissivities can be stored in a database with which the determined sensitivity and/or the determined transmissivity of the test device can be compared. Since the light receiving unit of the analysis device is the object under inspection during determination of transmissivity, the analysis unit of the analysis device can be used for determination of the transmissivity or another analysis unit can be connected with the light receiving unit for test purposes.

Preferably the test object comprises at least one substance or at least two substances selected based on the emission spectra. In doing so, an analysis result of high significance can be created, if, as an example, the substances create light features similar to the species that are expected in the tissue, that shall be treated and/or if—from the accuracy with which light features and/or signatures thereof can be determined from the test light appearance to which the substances contribute—the accuracy can be extrapolated with which the light features and/or signatures of the intervention light appearance and/or the species that contribute to the intervention light appearance.

The test object can have a predefined composition. Preferably the test object, particularly the composition and/or content of the test surface, can be selected based on the clinical indication for the surgical intervention, e.g. based on the "assumed" disease of the (assumed) tumor and/or the tissue to be treated.

The test object preferably comprises specific substances that also appear and/or are expected in the tissue to be examined and/or to be treated in order to create a test light appearance from which light features can be determined that can also be created based on the light appearance (intervention light appearance) created by the influence of the instrument on the tissue during the RF surgical intervention.

Preferably the electrode that the user places in the proximity of the counter electrode for creation of the test light appearance is specifically selected due to its composition for the creation of the test light appearance. For example, the electrode can be selected based on the expected contribution of the substance or material of the electrode to the test light appearance and/or the light appearance and/or based on one or more light features of the test light appearance and/or the light appearance, the light features being present due to the composition of the electrode. The electrode can be selected with regard to expected contributions to the test light appearance and/or the light appearance due to the composition of the electrode depending on the clinical indication for a surgical intervention.

The test object can comprise at least two different test surfaces. The test surfaces can distinguish with regard to their form, composition, physical state (solid, liquid) etc. The composition of the test surfaces can particularly distinguish in the type of species and/or their absolute and/or relative amounts. In doing so, the influence of the electrode and/or the electrode material can be determined and/or can be eliminated by calculation from an analysis result of the test light appearance and/or the intervention light appearance. The test surfaces can distinguish in that they consist of different materials. For example, the test surfaces can contain different metals, particularly pure metals or alloys, different solutions in the same or different materials, e.g. sponge or fleece materials. The test can comprise that a test light appearance is subsequently created against at least two different test surfaces.

The test device is preferably configured to determine a calibration of the analysis device from specific light features of the test light appearance. For example, the specific light features can be compared with light features stored in a database in order to determine the calibration of the analysis device. Preferably at least one parameter of the test device, the analysis device, particularly the light receiving unit and/or the analysis unit, the RF surgical instrument and/or the RF surgical apparatus is selected or modified based on the calibration. Preferably the system is configured to select or modify at least one parameter of the test device, the analysis device, particularly the light receiving unit and/or the analysis unit, the RF surgical instrument and/or the RF surgical apparatus or any other device or component of the system based on the calibration.

Preferably at least one value or value range of at least one parameter—e.g. a control and/or evaluation parameter of the test device, the test object, the analysis device and/or the RF surgical device, particularly the RF surgical instrument or an RF surgical apparatus for supply of the RF surgical instrument—is defined due to the test of the test device based on the test light appearance. Particularly, due to the test with the test device, a value or value range of a parameter of at least one of the indicated devices of the system can be defined based on the test light appearance that influences the operation of the system consisting of the indicated devices during treatment of tissue. Obviously this would be preferably a value or value range of a parameter that allows the desired RF surgical treatment result, but results in an improved analysis of the intervention light appearance by means of the analysis device.

The test object is preferably configured to define a minimum distance between an electrode that is located by the user of the test device for creation of the test light appearance in the proximity of the counter electrode and a test surface of the test object between which the test light appearance shall be created.

Preferably the test device is configured to define the atmosphere, particularly the composition and/or pressure thereof between an electrode and the test surface and/or counter electrode. For example, an argon atmosphere can be created between the electrode and the test object.

The test object is preferably configured to define an orientation of an electrode that is placed in the proximity of the counter electrode for creation of the test light appearance and/or the orientation of a light receiving unit relative to the test surface. For example, this can occur in that the test object is configured to guide the instrument and/or light receiving unit during insertion of the instrument and/or the light receiving unit in the test object, such that the instrument and/or light receiving unit automatically takes a position such that the instrument and/or light receiving unit have the defined orientation relative to the counter electrode.

The test device preferably provides a shield of the light receiving unit from the environmental light during capture of the light of the test light appearance.

The measures mentioned above serve individually or in any (sub-)combination to create conditions for the test in order to gain a particularly meaningful test result.

The test device is preferably provided for an instrument and an analysis device that can be combined by the user of the instrument, e.g. a surgeon, a surgery assistant or another member of the surgery team, for preparation of a surgery with the instrument or during surgery with the instrument. Instrument and light receiving unit of the analysis device can be preferably attached to one another by the user of the instrument prior to the surgery and/or during surgery in order to define the position of the light receiving unit of the analysis device relative to the instrument. Especially in such a surgery system comprised of instrument and analysis device that can be attached to one another by the user of the instrument, a non-operational analysis device may result and/or an analysis device can result that requires a specific adjustment of the RF surgical device and/or the analysis device to make the analysis device operable, due to an erroneous handling, damage, contamination, non-fitting of the instrument and the analysis device. Such cases can be discovered and corrected due to tests with the test device.

Thus, according to embodiments of the invention, a system is provided that comprises a device for attachment of a light receiving unit of an analysis device on the instrument or component of the instrument. The device is preferably configured such that the light receiving unit can be connected with the instrument, particularly preferably during surgery, by the surgical user of a surgical instrument or his/her assistant.

For example, the device can be an adapter in which or on which an optical fiber is attached or can be attached forming the light receiving unit. The adapter can be connected with the instrument, e.g. a handle of the instrument, in order to define a position of the light receiving unit relative to an electrode of the instrument. By means of the test device it can be checked whether the light receiving unit combined with the instrument in this manner operates correctly.

The method according to embodiments of the invention is a method for testing, particularly calibrating an analysis device for analysis of light appearances that are created by an RF surgical instrument during influence on biological tissue. The method comprises the creation of a test light appearance between an electrode and a test object that is not a human or animal body and the capture of light of the test light appearance by the light receiving unit. The method is therefore particularly not carried out on the human or animal body. The method can be carried out with a test device described herein and/or a system described herein having a test device and an RF surgical device. Particularly, individual or multiple arbitrary method steps can be carried out by or by means of a test device described herein and/or a system described herein. The user of the analysis device can carry out testing by means of the test object provided for this purpose instead of misusing an object or to carry out the test, even on the patient, particularly to make sure of the operability of the analysis device or to adjust it.

The method can be carried out directly prior to surgery for preparing a surgery or during surgery, namely by the user of the instrument, e.g. a surgeon or a surgery assistant. The test device, particularly the test object is preferably configured for use by a physician who intends to carry out a scheduled (planned) surgery with the RF surgical instrument or an assistant of the physician for preparing surgery and/or during surgery.

In an embodiment of the method at least one test light appearance can be created and evaluated between one electrode and at least two different test surfaces respectively.

For testing preferably the system is used comprising the RF surgical instrument, RF surgical apparatus and analysis device that is also used for surgery.

Preferably identical adjustments for the instrument are made for testing or testing is carried out with the same adjustments that shall also be used for the surgery with the instrument and/or adjustments derived therefrom.

BRIEF DESCRIPTION OF THE DRAWINGS

Further advantageous features and embodiments are derived from the dependent claims as well as the following description and figures that schematically show by way of example:

FIG. 1*a* is an illustration of positioning of a light receiving unit positioned relative to an electrode or a light appearance during influence of the electrode on tissue, FIG. 1*b* is a schematic illustration of an electrode tip in the light acceptance cone of an optical fiber, FIG. 2a is an exemplary instrument in the form of a handle with an electrode arranged distally inserted into an adapter comprising a light receiving unit in form of an optical fiber, FIG. 2b is a section of a combination of an instrument and an adapter, as in FIG. 2a with a different electrode shape, FIG. 6a is a further embodiment of a test object, FIGS. 6b1 and 6b2 are a further exemplary counter electrode and electrode, respectively, FIG. 6c is an exemplary counter electrode.

DETAILED DESCRIPTION

Figure 3:
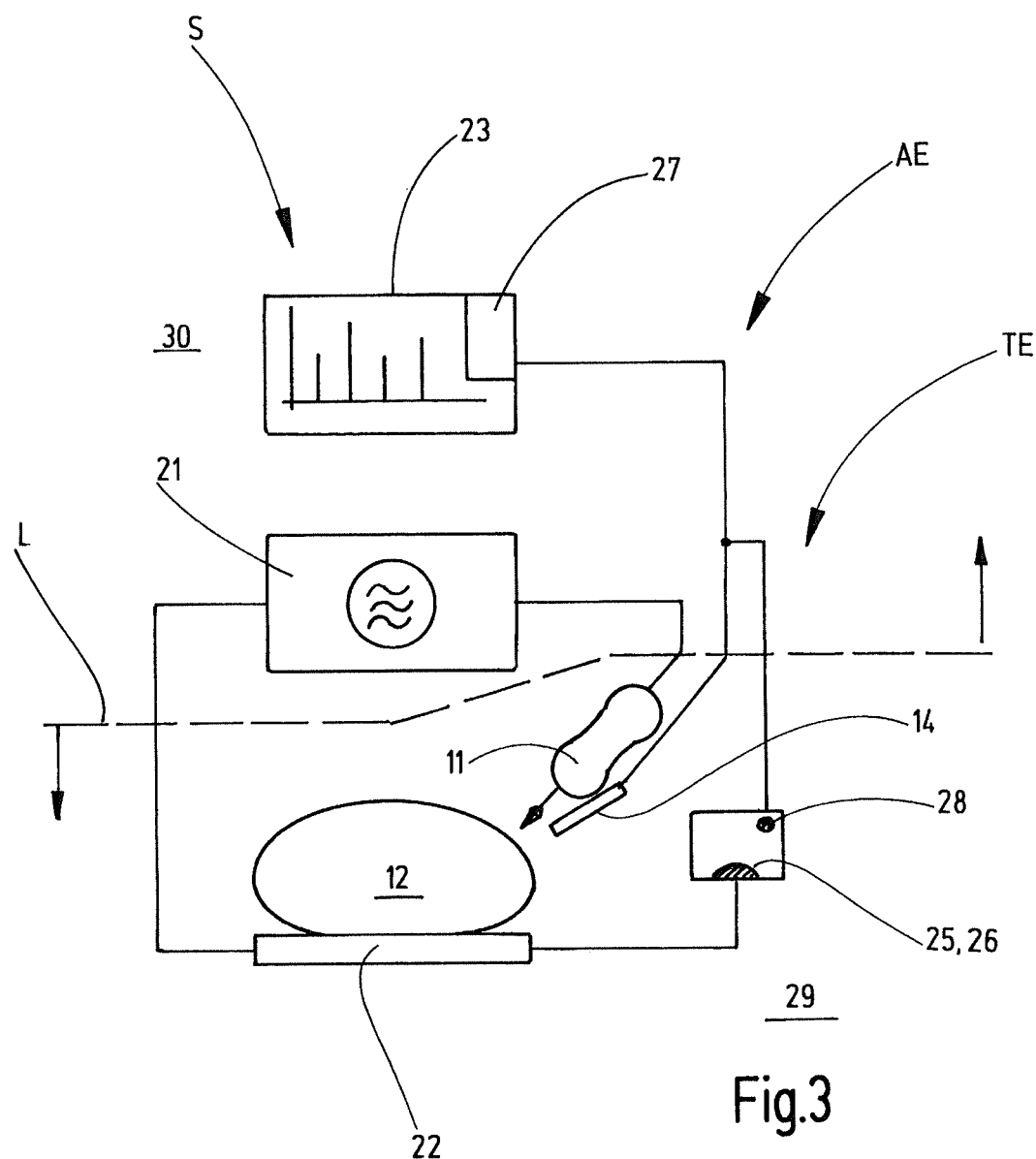
FIG. 3 is an exemplary embodiment of a system having an RF surgical device having an analysis device and a test device.

FIG. 1a shows an electrode 10 as it can be used in a surgical instrument 11, for example. The electrode 10 is arranged near tissue 12 to be treated of a patient. Means for holding the electrode 10, such as a handle, are for sake of clarity not shown in FIG. 1a. The electrode 10 comprises a shank 10a and a head or tip 10b, but can consist, for example, of titanium or tungsten. An insulation 10c is applied on the electrode 10 adjacent to the head or tip 10b to more accurately define areas of electrode 10 creating a plasma 13, particularly spark or light arcs between these areas and tissue 12. The electrode 10 used for creation of the plasma intervention light appearance 13 is preferably a partly insulated cutting electrode as used in radio frequency (RF) surgery. Electrode 10 preferably comprises burn-off resistance with regard to sparks corresponding at least to the burn-off resistance of titanium or tungsten.

An optical fiber 14 is arranged inside a hose 15 or a line 15 under an acute angle W relative to the electrode 10. The optical fiber 14 and hose 15 are fixed in their position relative to electrode 10. A light acceptance cone 16 is shown that contains all directions from which the optical fiber 14 can capture light and transmit light to an analysis unit (not shown in FIGS. 1a and 2) for the purpose of analysis of light. As illustrated, the tip or head 10b of electrode 10 within the light acceptance cone 16. This is also apparent from schematic sectional illustration through the light acceptance cone 16 in FIG. 1b. Light appearances 13 occurring between electrode 10 and tissue 12, such as a continuous plasma as in the case of argon plasma coagulation, a light arc or— where applicable—sparks forming and distinguishing in quick sequence are therefore created within light acceptance cone 16. The light thereof comprising infrared, visible and/or ultraviolet electromagnetic waves is thus partly captured by the optical fiber 14 and transmitted to the analysis unit.

Hose 15 serves for conducting a fluid, particularly gas, e.g. $CO_2$, to the distal end of hose 15 where it exits in direction toward electrode 10. The fluid flow serves for reducing contamination of optical fiber 14, for cleaning the optical fiber 14, for blowing away steam or particles forming due to the electrosurgical influence on tissue 12.

It is, however, possible that in spite of the exiting $CO_2$ flow that is limited in its flow rate to preferably maximum 1 liter/minute in order to not displace tissue 12 to be treated, particle or steams precipitate on the optical fiber 14 and limit the transmissivity of optical fiber 14. This limitation can potentially also occur only for specific wavelengths, e.g. in the infrared, visible and/or ultraviolet range of the electromagnetic spectrum. By contamination of electrode 10 the light inlet 17 of optical fiber 14 can be partly shaded. By contamination of electrode 10 the shape of the light appearance 13 can be partly modified, because due to contamination a part of tip or head 10b can be electrically insulated. Contaminations cannot only occur due to steams or particles flying away. It is also possible that the surgeon unintentionally touches tissue 12 with electrode 10. Because the ignition distance for igniting the light appearance between electrode 10 and tissue 12 that has to be established at most can be, for example, only a few millimeters between the distal end of electrode 10 and tissue 12, if the light appearance is ignited in an environment enriched with noble gas, e.g. argon, or even only a few tenths of a millimeter, if the light appearance is ignited in an environment enriched with $CO_2$. Contaminations can also result in a change of the spectrum of the light appearance.

How much light of the light appearance 13 can be captured by means of the optical fiber 14 depends highly from its position relative to electrode 10. For example, it depends from the distance A of the light inlet 17 from the tip of electrode 10 and/or the light appearance 13, the arrangement of the light inlet 17 around electrode 10 and the angle W between the optical fiber 14 and electrode 10, etc.

FIG. 2a shows an RF surgical instrument 11 in form of an RF applicator having a handle 11a and a preferably exchangeable electrode 10. The applicator 11 is plugged into an adapter 19. As an alternative, applicator 11 and adapter 19 can be attached to each other, e.g. side by side. The adapter 19 contains an optical fiber 14 arranged therein or thereon and can provide a channel 20 for output of a $CO_2$ stream. Adapter 19 serves to attach optical fiber 14 and instrument 11 to one another. The surgeon or another member of the surgery team can connect adapter 19 with instrument 11, e.g. during surgery.

Adapter 19 supports the definition of the position of the optical fiber 14 relative to electrode 10. However, many variation possibilities remain. For example, electrode 10 is preferably exchangeable. Different forms of tip or head 10b of electrode 10 are possible. For example, needle shaped and spatula-shaped electrodes 10 are known. FIG. 2b illustrates, for example, a hook-shaped electrode 10 instead of electrode 10 illustrated in FIG. 2a. Also the electrodes 10 can have different positions and thus protrude with different lengths from adapter 19. The position, i.e. the distance and/or orientation of the light inlet 17 relative to electrode 10 and thus also the position of the light appearance 13 relative to the light acceptance cone 16 depends, however, on the form and length of the longitudinal part of electrode 10 protruding from adapter 19.

The definition of the position of the optical fiber 14 relative to electrode 10 is then particularly reliable, if the RF applicator 11 fits the adapter 19. It is, however, considerable that unintentionally or intentionally an RF applicator 11 is used to which the adapter 19 does not fit. Then a correct position of the optical fiber 14 relative to electrode 10 is potentially not guaranteed anymore.

It also has to be mentioned that the light receiving unit, e.g. optical fiber 14, can be damaged. Also coupling pieces between light receiving unit 14 and analysis unit or in case of multiple part light receiving units 14 between parts of the light receiving unit 14 can be defective and result in an affected transmission of light.

Electrode 10 or instrument 11 are supplied with electrical energy by means of an RF (radio frequency) generator (not shown in FIGS. 1a and 2). The standard allows a standard deviation of the RF output power for RF generators of +/−20%. Depending on the desired RF surgical intervention, e.g. cutting, coagulating, devitalizing, thermo-fusing, etc. different powers, wave shapes of the RF voltage supplied to electrode 10, etc. are required. The characteristics of the RF voltage supplied to electrode 10 are denoted as mode or operating mode. The operating mode influences light emission of the RF light appearance 13, e.g. the RF spark, on biological tissue 12.

In addition, the specific electrical resistance of biological tissue 12 varies considerably. Fat tissue has, for example, approximately $3.3 \cdot 10^7$ Ohm mm$^2$/m, muscle tissue $2.0 \cdot 10^6$ Ohm mm$^2$/m and blood only $1.6 \cdot 10^6$ Ohm mm$^2$/m on the contrary. Also the medium (aerosol, air mixture) between electrode 10 and tissue 12 can highly depend on the application. Depending on whether the intervention is carried out in an open surgery manner, endoscopically or laparascopically, the humidity between electrode 10 and tissue 12 can vary considerably. The ignition capability (ionization) of plasma 13 is very highly influenced by the humidity or liquid on the active electrode 10. The atmosphere between electrode 10 and tissue 12 can be partly determined by the RF surgery device, depending on whether, for example, argon gas or $CO_2$ gas is output in the region between electrode 10 and tissue 12. The breakdown voltage depends on the type of gas. For example, if the spark 13 is ignited in the argon atmosphere, it is different compared to the case where spark 13 is ignited in dry air or in a $CO_2$ atmosphere.

Summarizing it can be determined that the type of the light appearance 13 or light features thereof, particularly its shape, intensity, spectral composition, etc. depend on very highly on the individual conditions for a specific surgery intervention and can change in the progress of the intervention. How much light—also depending from the wavelength—created by the light appearance 13 can be captured by the optical fiber 14 and/or can be transferred into an electrical signal in the analysis device also highly depends on the conditions during surgery.

A concept improved according to embodiments of the invention for a system S for RF surgical treatment (particularly cutting and/or coagulating) of tissue 12 under use of optical emission spectroscopy is schematically illustrated by way of example in FIG. 3. System S (RF surgical system) comprises an RF surgical apparatus E having an RF surgical instrument 11—here in form of an applicator 11 having a handle 11a and an electrode 10 attached on the distal end of handle 11a—and an RF generator 21 for supply of instrument 11. The RF surgical apparatus E is an apparatus for monopolar RF surgery in which the current circuit is closed via a neutral electrode 22 that is attached to the patient. As an alternative or in addition, the RF surgical apparatus E is configured for bipolar RF surgery.

System S further comprises an analysis device AE for analysis of light appearances, particularly continuous plasma, light arcs, sparks, between electrode 10 and tissue 12 of the patient's body by means of optical emission spectroscopy in the infrared, visible and/or ultraviolet range of the spectrum. The analysis device AE comprises an optical fiber 14 as light receiving unit and an analysis unit 23 that is connected with optical fiber 14. The optical fiber 14 can be attached to the instrument 11 by means of an adapter 19 similar to FIG. 1a. The light signal transmitted by means of the optical fiber 14, from the location at which the intervention is carried out, is converted by system S into an electrical signal.

The test device TE for testing, particularly calibrating of analysis device AE comprises a test object 24 that provides a counter electrode 25 with a test surface 26. By means of instrument 11, a plasma test light appearance in form of a spark or a continuously maintained plasma between instrument 11 and test object 24 can be created. Test object 24 is in so far configured for creation of a plasma test light appearance. A counter electrode 25 can have the same electrical potential as the neutral electrode 22. The counter electrode 25 can be connected with RF generator 21 via neutral electrode 22, for example. Test device TE further comprises an evaluation unit 27. This evaluation unit 27 can be integrated together with the analysis unit 23 in one apparatus or can be part of the analysis unit 23. The analysis unit 23 and/or evaluation unit 27 can be integrated in different apparatus. The analysis unit 23 and/or the evaluation unit 27 can also be distributed over multiple apparatus and can be, for example, formed by one or more software modules that are executed in one apparatus or multiple apparatus. The test device TE can further comprise a signaling unit 28 for optic and/or acoustic and/or haptic output of a message to the user of system S. The signaling unit 28 is connected with evaluation unit 27 in order to be initiated by the latter as applicable for the output of the message.

The sterile area 29 of the operating room separated from a non-sterile area is shown by dashed line L. As illustrated, test device TE is arranged partly in sterile area 29. Particularly the test object 24 is arranged inside sterile area 29.

By means of test device TE, according to FIG. 3 it can be checked whether system S, particularly analysis device AE is operable and/or system S, particularly analysis device AE can be adjusted in order to be able to operate with system S or analysis device AE. Particularly, it can be preferably checked whether a tissue distinction by means of optical emission spectroscopy on light appearances created by influence with an electrode 10 on tissue 12 can be carried out by means of the analysis device AE. As an alternative, an adjustment for the system S, particularly analysis device AE, can be determined by means of the test device TE by means of a test, such that it can operate with a predefined accuracy.

Figure 4:
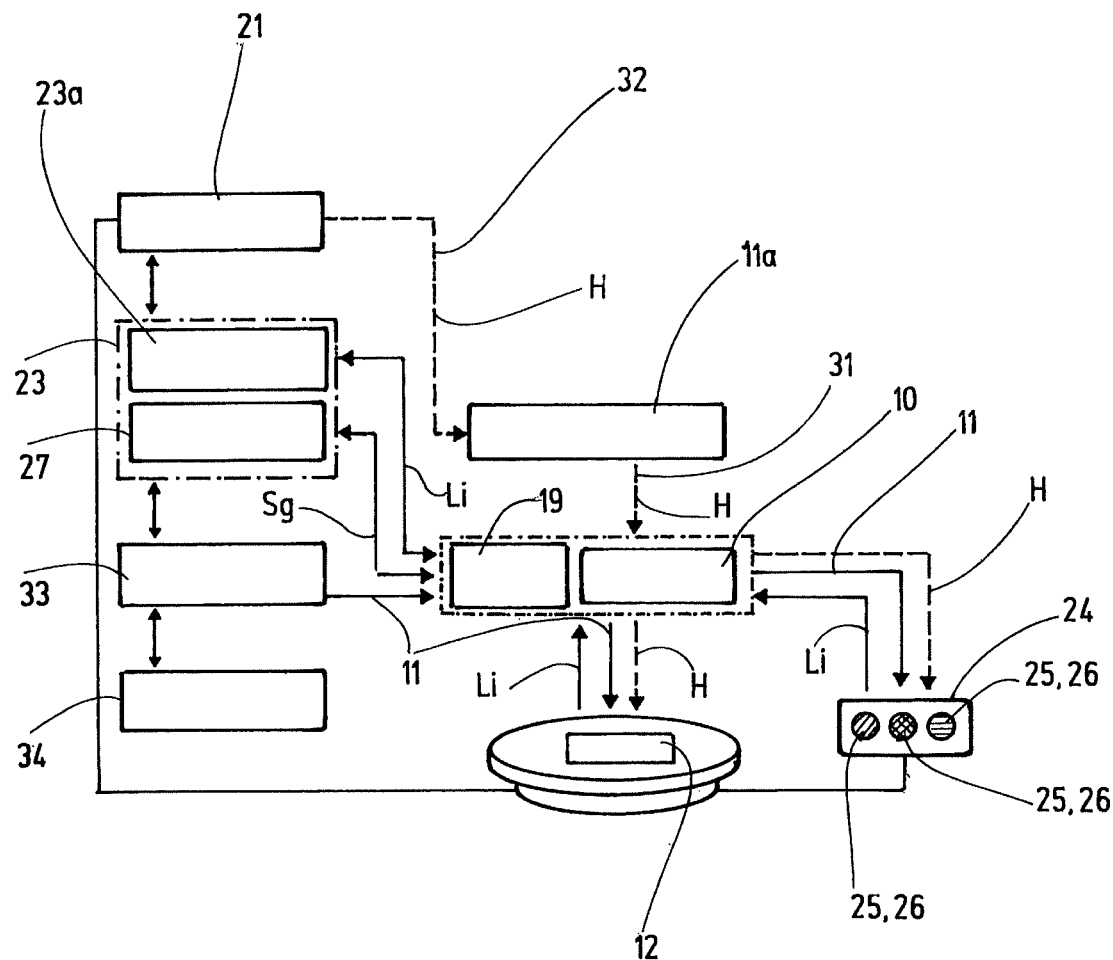
FIG. 4 is a further embodiment of a system having an RF surgical device, an analysis device as well as a test device.

FIG. 4 illustrates a system S for RF surgery by using optical emission spectroscopy. The embodiment according to FIG. 4 can be a specification of system S according to FIG. 3 or a different embodiment of the inventive system S. FIG. 4 illustrates flows of media, powers and signals (RF current H, light Li, status signal Sg and flushing medium M (e.g. $CO_2$)). RF electrode 10 is supplied with electrical RF energy via a line 31 in the handle that is connected with the RF surgical apparatus 21 via a line 32. An RF current flows between RF electrode 10 and body 12 of a patient. Thereby a light appearance 13 is created, whereby light is captured by the optical fiber 14 and is supplied to an analysis unit 23. A flushing medium, particularly $CO_2$ is output to the intervention location between electrode 10 and tissue by means of a flushing system 33. Flushing system 33 is controllable by means of a foot switch 34. The RF surgical apparatus E is controllable by means of buttons 35 (see FIG. 2a) on the handle 11a and/or on the surgical apparatus 21.

In case of a test with the test device TE, a current flows between electrode 10 and a test surface 26. Flushing medium can be output in order to create a defined atmosphere between electrode 10 and test surface 26. Light of a light spark is captured by a light receiving unit 14 and transmitted to the analysis unit 23. The analysis unit 23 can output status signal to the RF applicator 11 or adapter 19.

As shown in FIG. 4, the test device TE can comprise multiple test surfaces 26. The test surfaces 26 can distinguish from one another. The test surfaces 26 can particularly distinguish in their composition, form, size, phase of test surface 26 (e.g. liquid, solid), etc. Each test surface 26 can comprise an alloy or pure metal (purity larger or equal to 95%). Alloys of different test surfaces 26 can distinguish from one another and/or the pure metals that are contained in the different test surfaces 26 can distinguish from one another.

Figure 5:
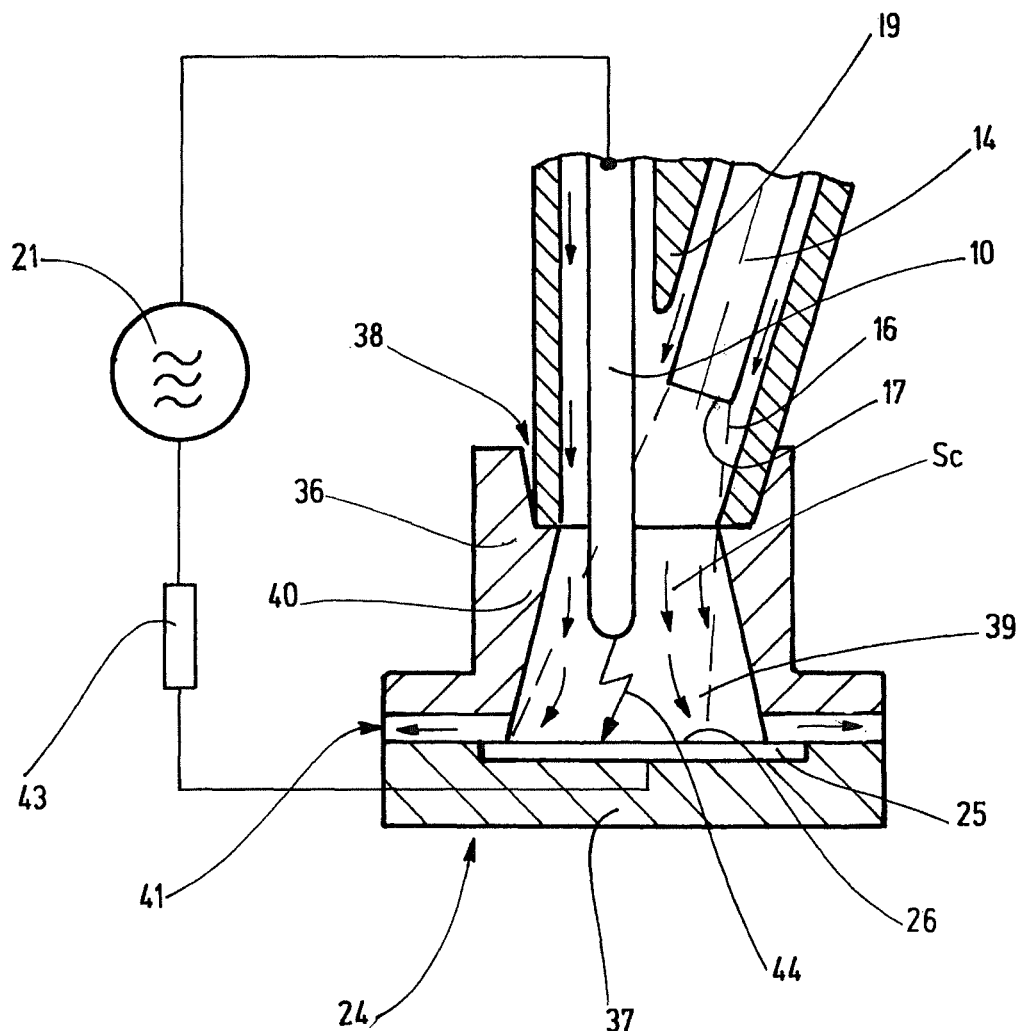
FIG. 5 is an embodiment of a test object.

FIG. 5 shows an exemplary test object 24 in a sectional illustration. For example, test object 24 can be used in the system according to FIGS. 3 and 4. Test object 24 comprises a spacer 36 and a support 37 for the test surface 26. The test surface 26 is provided by a reference electrode or counter electrode 25. The counter electrode 25 can be a metal plate or metal foil, for example.

Spacer 36 provides an opening 38 in which the adapter or the instrument 11 can be inserted or on which or against which the adapter or the instrument 11 can be placed. Due to the spacer function, it is guaranteed that the distance between instrument 11, handle and/or adapter and the test surface 26 does not exceed a maximum value.

Preferably opening 38 is configured to guide instrument 11, adapter 19 and/or electrode 10 and/or light receiving unit 14 in order to define a specific position of electrode 10 and/or light receiving unit 14 relative to the counter electrode 25. Preferably the shape of opening 38 on one hand and the shape of instrument 11, electrode 10 and light receiving unit 14 and/or adapter 19 on the other hand, are adapted to one another such that the position of instrument 11, light receiving unit 14, electrode 10 and/or adapter 19 is defined relative to the test surface 26, if the shapes are engaging one another.

Between opening 38 of spacer 36 and test surface 26 a space 39 (plasma space) is formed for the plasma. The space 39 is formed by electrically insulating walls 40 (except for the counter electrode 25). Test object 24 comprises at least one outlet opening 41, through which gas can be output that flows out of the adapter into space 39, such that a specific pressure of inert gas Sc, for example $CO_2$ or argon, is maintained or a specific pressure is not exceeded. For example, line 15 in the adapter 19 can be supplied with argon for the purpose of the test. In addition, the outlet opening 41 provides for a constant atmosphere by continuous exchange of the medium in the space 39. As apparent from FIG. 5, electrode 10 that forms part of the RF instrument 11 in combination with light receiving unit 14 protrudes over the distal end of instrument 11 or adapter 19 into space 39 for the plasma. The light inlet 17 of optical fiber 14 is offset backwardly relative to the outlet 42 (see FIG. 2a) of adapter 19 or instrument 11.

Counter electrode 25 can be connected with the RF generator 21 via a series resistor 43. The electrode 10 is also connected with RF generator 21 in order to be supplied therefrom with RF energy. In doing so, the light appearance (test light appearance) 44 between tip 10b of electrode 10 and counter electrode 25 is created.

The material for the counter electrode 25 or test surface 26 can be specifically selected based on the clinical indication for the RF surgical intervention. For example, the material can comprise species that are also expected in the tissue 12 to be treated, particularly to be cut and/or coagulated, i.e. treated during the RF surgical intervention.

Figure 6:
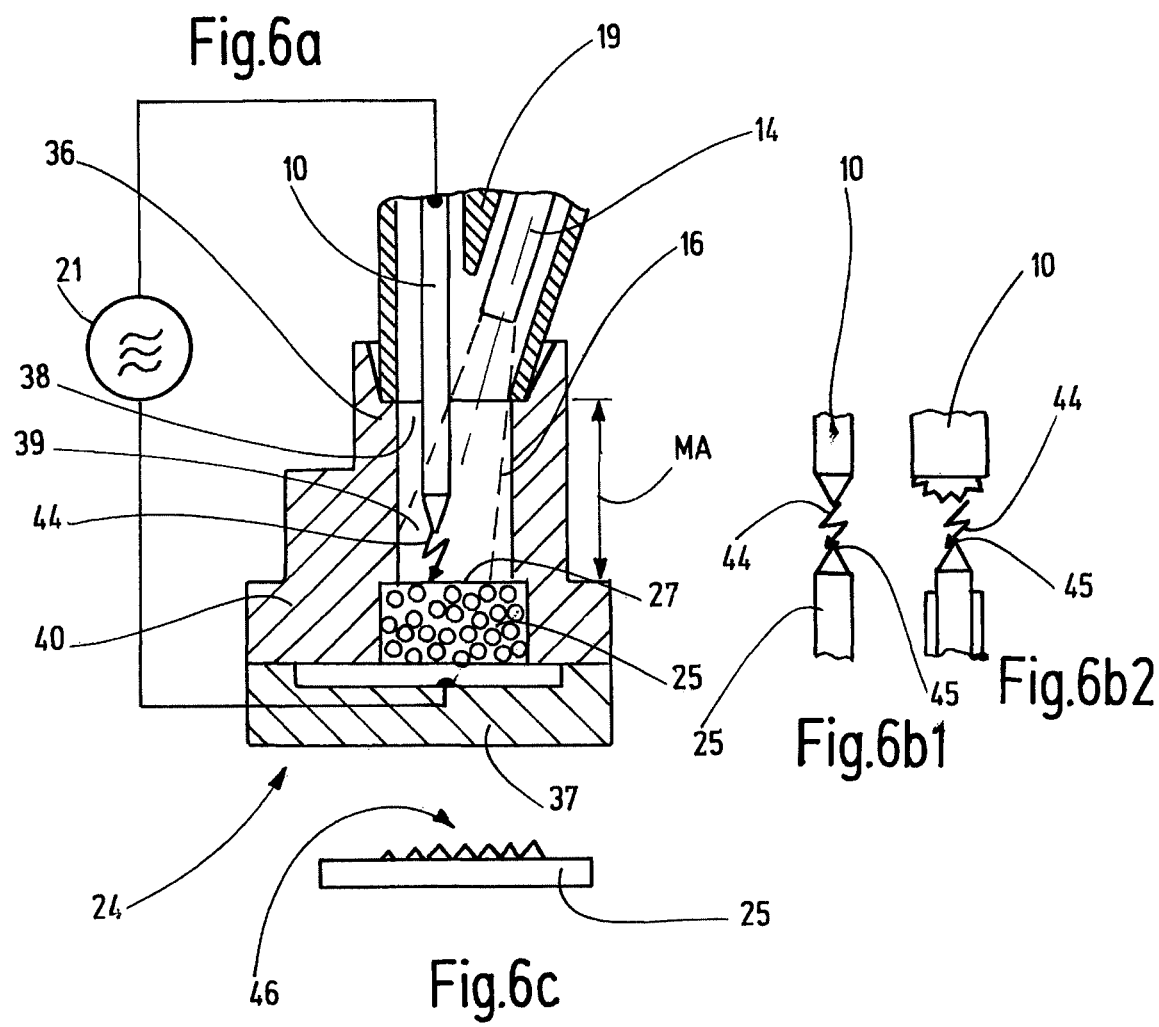

FIG. 6a shows an alternative embodiment of a test object 24. For example, test object 24 can be used in the system according to FIG. 3 or 4. The test surface 26 is here formed by a sponge or fleece 25 wetted with a reference solution, particularly saline solution. In doing so, a test surface 26 can be created that comes close to the real tissue 12. Substances can be specifically introduced in the solution that shall be proved and/or distinguished for test purposes by means of the test device TE. The solution and/or substances can be specifically selected based on the clinical indication for the RF surgical intervention. In doing so, for example, a distinction of species and thus a "tissue" distinction can be carried out for test purposes not on the body of the patient, but on an exogenous material. The reference solution can be specifically selected based on the medical indication of the surgical intervention, e.g. because a specific reference solution contains species that are amongst others or in the specific composition expected in the tissue 12 that is partly transitioned into the plasma condition during the RF surgical intervention and for this reason contributes to light features to the intervention light appearance 13.

The test surface 26 can be a substantially planar surface, as in the examples according to FIG. 5 and FIG. 6a. A counter electrode 25 can alternatively comprise a tip 45, as in the embodiments according to FIGS. 6b1 and 6b2. For example, electrode 10 can comprise a round spatula shape (FIG. 5), a pointed shape (FIG. 6a, FIG. 6b1) or a spatula shape with pointed forms (FIG. 6b2). Electrode 10 can comprise an insulation that keeps the tip or head of electrode 10 non-insulated. FIG. 6b3 shows an example of a counter electrode 25 as metal plate having grooves 46. By means of the electrode shape and the counter electrode shape, the contour of the test light appearance 44 can be predetermined in order to obtain a meaningful test result.

Preferably the counter electrode 25 is burn-off resistant, if it is considered for multiple use. Preferably the burn-off resistance is, however, less than that of electrode 10. Preferably test device TE can be sterilized. Test device TE, particularly test object 24, can be configured for multiple use. A test object 24 or a counter electrode 25 as single-use product is preferably formed by means of a wetted sponge or fleece 25.

Figure 7:
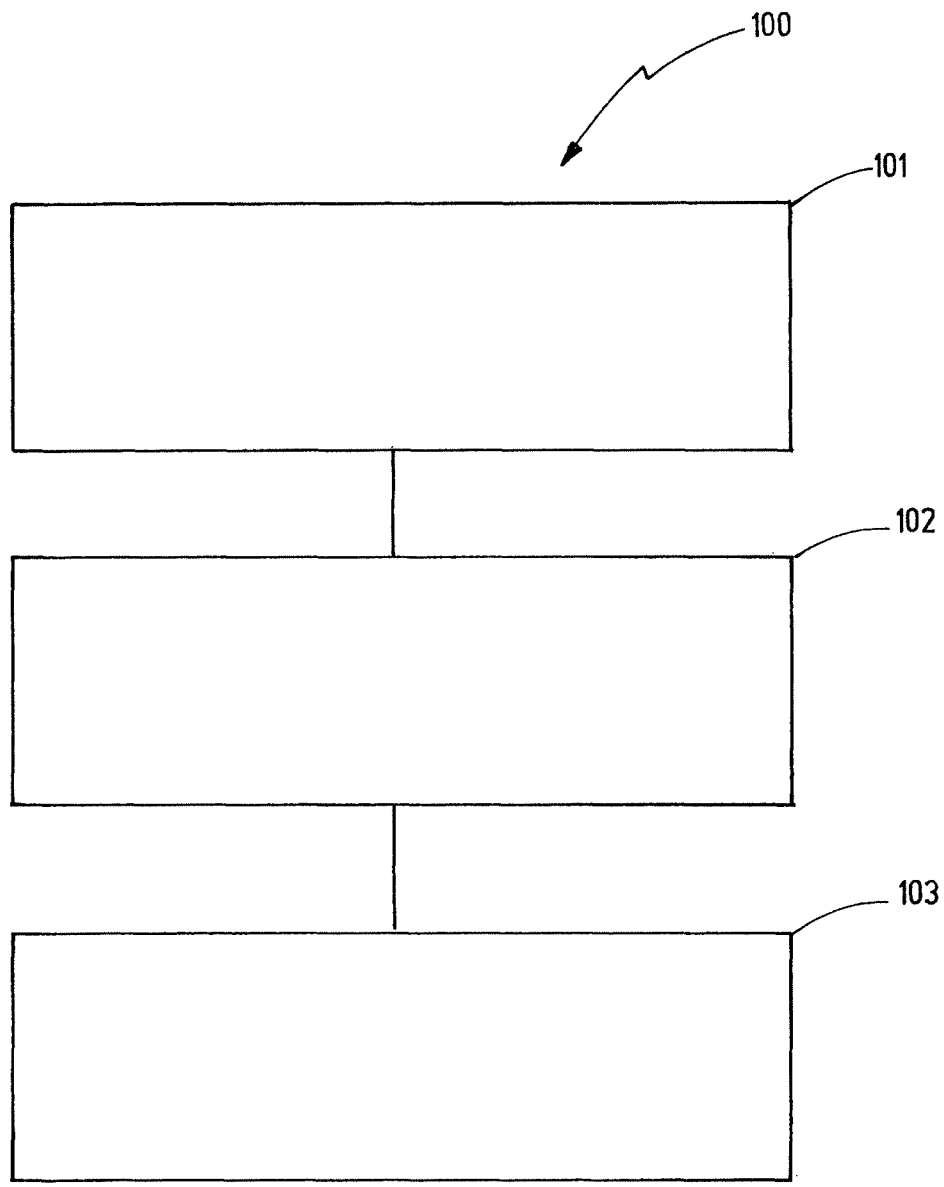
FIG. 7 is an embodiment of an inventive method.

By means of at least one of the described embodiments of system S according to the invention, it can be operated as follows, for example:

System S, for example according to FIG. 3 or 4, can be composed foremost by the surgery team for the planned intervention. Particularly the instrument 11 and/or electrode 10 and/or test object 24 and/or test surface 26 or counter electrode 25 could have been selected for the intervention based on the clinical indication. For preparation of the intervention or during the intervention the user of the analysis device AE can carry out a function test of the analysis device AE in that the user creates a test light appearance 44 between electrode 10 of instrument 11 and counter electrode 25 by means of instrument 11 (step 101 of the embodiment of method 100 according to FIG. 7). Possible results of the function test can be, for example, "operative" or "non-operative". The user can insert the instrument 11 into opening 38 of test object 24 or place instrument 11 on opening 38 for this purpose. Test device TE can be configured to recognize, if instrument 11 is combined with test object 24 for the purpose of creation of a test light appearance 44. For example, test device TE can be configured to recognize, if instrument 11 or adapter 19 is inserted into opening 38 or brought in abutment. Preferably test device TE can select specific adjustments of system S, particularly RF surgical apparatus E, based on the recognition of an intended test. For example, test device TE can exclude specific adjustments of system S for the test that are otherwise possible or can allow adjustments that are otherwise impossible. As an alternative or in addition, test device TE is configured such that the surgery team can switch system S in a test mode by means of an operation element (not shown). The user can initiate the creation of the test light appearance 44 himself/herself or the test device TE can automatically trigger the test. Test device TE can comprise means (not shown) for determination of a position of electrode 10, instrument 11 and/or adapter 19 on test object 24 or in test object 24. In doing so, for example, it can be automatically determined, for example, whether electrode 10, instrument 11 or adapter 19 is arranged in a distance from test surface 26 such that the creation of a test light appearance 44 is automatically triggered or manual triggering is allowed. Test device TE can be configured to automatically select a suitable adjustment for creation of the test light appearance based on the conditions of the test (e.g. used electrode 10, instrument 11, RF surgical apparatus 21, type of counter electrode 25, etc.). The test adjustments or test adjustment possibilities are selected, such that the RF electrode 10 or the optical fiber 14 are not damaged during the test. The RF voltage between electrode 10 and counter electrode 25 is preferably selectable, for example. This depends particularly from the shape of electrode 10, from the distance of the electrodes 10 from one another, from the material of the electrode 10 and counter electrode 25 and from gas surrounding electrode 10 and counter electrode 25 in the test object 24. As an alternative or in addition, the creation of the test light appearance 44 can use substantially the same adjustment of system S as for the actual RF surgical intervention.

Due to triggering of the test, a plasma test light appearance 44 is created, e.g. a stationary plasma as during argon plasma coagulation, a light arc or a spark between electrode 10 of instrument 11 and counter electrode 25 in that a high voltage impulse ionizes the atmosphere between electrode 10 and test surface 26 and thus makes it electrically conductive. In doing so, the path becomes low impedance and a current flow of several Ampere can occur. During spark excitation the current flow is again interrupted after a few microseconds, for example, however is restarted again after a break period. The spark sequence depends on the repetition frequency of the generator, e.g. 20 kHz. The current form of the voltage source can be a pure sine, for example 350 kHz, or a modulated sine wave form. A single pulse, a pulse packet with multiple oscillations, that have a repetition frequency in each case, can be used such that plasma is maintained, for example. During creation of the test light appearance 44 or the intervention light appearance 13 (a light appearance created due to the actual intervention on tissue 12 of the patient with electrode 10 can be denoted like this) a voltage, power or plasma feedback control can be used. In case of the plasma feedback control (also denoted as light arc feedback control) one or more plasma features, e.g. specific harmonics, are kept constant or within a range.

Light of the test light appearance 44 is partly captured by the light receiving unit 14 (step 102) and transmitted to a device 23a (compare FIG. 4) of the analysis unit 23 that is configured to convert light transmitted via the optical fiber 14 into an electrical signal that is transmitted to the test device TE for the further evaluation by means of the evaluation unit 27. For example, the device 23a can compose the light, like a spectrometer, in a wavelength depending manner in individual amounts to one or more electrical signals.

In order to evaluate the operability of the analysis device AE, the signal power can be determined based on the test light appearance 44, for example, being the signal power reaching the evaluation unit 27. For example, the evaluation unit 27 can compare the power, e.g. the total power or wavelength depending intensities, with reference values in order to evaluate the transmission of light of the test light appearance 44 up to the device 23a for converting the light signal into an electrical signal. Thereby the energy input based on the RF voltage and the RF current for the creation of the test light appearance 44 can be considered.

The test is particularly meaningful, if the electrode 10 is orientated relative to the test surface 26 or counter electrode 25 and/or the position of electrode 10 relative to the test surface 26 and/or counter electrode 25 is defined by means of the test object 24. Alternatively or additionally, the adapter 19 can be aligned relative to the test surface 26 or counter electrode 25 and/or the position of adapter 19 relative to the test surface 26 and/or counter electrode 25 can be defined by means of the test object. If the test light appearance should be too weak, for example, or even not be ignited, this can indicate a non-suitable position of optical fiber 14 relative to electrode 10. This is one example of how operating errors or other errors in combining the optical fiber 14 with instrument 11 or an equipment of instrument 11 with an electrode 10 not suitable for light analysis can be discovered by means of the test device TE.

If test object 24 is configured to keep away external light coming out of the environment from the light inlet 17 of the light receiving unit 14 during the test, the significance of the test can be increased in addition or as an alternative. Based thereon, environmental light is not captured, wherein this means that at most a light amount coming out of the environment is captured that does not affect the test with the test device TE. As an alternative or in addition, the test device TE can be adapted to an operation field illumination (not illustrated). The analysis unit 23 and/or evaluation unit 27 are preferably non-sensitive in the spectral range in that the operation field illumination operates. In this manner blinding of evaluation unit 27 and/or analysis unit 23, particularly a discriminator unit thereof (not shown) is avoided, wherein the discriminator unit serves for assigning of light features to tissue features in order to be able to make a tissue distinction by means of the analysis device AE.

For a defined plasma creation, particularly spark excitation, a defined atmosphere in which the excitation occurs, such as an argon atmosphere with high purity, is of advantage. Low PPM oxygen as well as steam or vapors of organic compounds within the argon that are always present in biological tissue 12 can disturb the discharge severely. For this reason an atmosphere is preferably defined by means of the test device TE in which the plasma for creation of the test light appearance 44 is ignited. This refers particularly to the composition and/or the pressure of the atmosphere. The test object 24 provides an ignition space (plasma space) 39. For example, the plasma space 39 in the test object 24 is flooded during the execution of the test with gas, e.g. $CO_2$ and/or argon. In the ignition space 39 a constant pressure can be provided. If the spark creation is carried out under inert gas conditions (e.g. argon gas), other influences from the environment (operation micro climate) can be largely inhibited. By means of noble gas, e.g. argon, the signal strength of the light emission can be positively amplified. For example, the test object 24 can comprise a connection (not shown) for supply of plasma space 39 with argon such that, for example, the creation of the test light appearance 44 the plasma space can be flooded or is flooded with noble gas, particularly argon, whereas the flushing device otherwise operates with $CO_2$, for example, particularly during RF surgical intervention.

According to embodiments of the invention, the specific analysis device AE can be tested that shall be used or is used for analysis during surgical intervention. Particularly the specific light receiving unit 14 and the analysis unit 23 can be tested for operability and namely based on a plasma test light appearance 44 between electrode 10 used during the intervention and a counter electrode 25 without influence on the body of the patient. Thus, the test conditions come very close to the actual use based on the use of largely identical components as well as an ignited plasma as in the actual intervention by application of electrode 10 of instrument 11. By means of the test, a non-suitable position of the optical fiber 14 relative to electrode 10, e.g. due to incorrect seating of the handle in the adapter, the use of a non-suitable electrode 10, a contaminated or damaged optical fiber 14, an insufficient coupling between sections of the optical fiber 14 or between the optical fiber 14 and device 23a for converting of the light signal in an electrical signal can be excluded. Also a shading, due to a potentially contaminated electrode 10, an unfavorable form of the test light appearance 44 (and thus potentially of the intervention light appearance 13) due to contamination or an unfavorable electrode shape can be excluded. By means of the test device TE it can be tested whether the signal strength is sufficient and can be used for a meaningful evaluation of the captured light signal during the analysis of the light features created by the intervention light appearance 13 due to the RF intervention on the tissue 12.

For excitation of test light appearance 44, preferably the RF generator 21 of the RF surgical apparatus E is used that also supplies electrode 10 during intervention on tissue 12 of the patient. For this the sample to be analyzed (test surface 26, counter electrode 25) and the RF electrode are connected with generator 21.

The test device TE can submit a status signal to the surgical user by means of a signaling unit and optical, acoustical and/or tactile manner (e.g. "analysis device operable" or "analysis device non-operable").

Test device TE can be configured to recommend measures to the user where appropriate in order to allow an improvement of the analysis by the analysis device AE, particularly in order to obtain a stronger signal. For example, the test device TE can determine for this purpose a probability for one or multiple limitations with regard to their responsibility for the potentially negative test result.

By means of the test method 100, a wavelength dependency of the transmissivity of the light receiving unit 14 can be determined in the context of calibration and where applicable, one or more corrections/correction factors can be determined that can be considered during evaluation of the signal based on the test light appearance 44 and/or of the signal based on the intervention light appearance 13. Determination and/or consideration can be automatically carried out by the test device TE and/or the analysis device AE.

In order to determine the wavelength dependency of the transmissivity, preferably a test light appearance 44 is created in the spectrum of which two or more spectral lines are present and/or multiple test light appearances 44 are created in the spectrum of which at least one spectral line is present in each case, wherein at least one of the spectral lines of a test light appearance 44 distinguishes from the other test light appearance 44. Such test light appearances 44 can be specifically created, if the composition of the test surface 26 is selected based on the kind of species in the composition—and thus the characteristic spectral lines—as well as their frequency of occurrence.

Based on the plasma that is created for creation of the test light appearance between electrode 10 and counter electrode 25, material of the counter electrode 25 and/or electrode 10 is removed (evaporated, atomized and ionized) and in so doing, species (atoms, molecules, ions thereof) are created from the material of counter electrode 25 and electrode 10 that now also occur in the plasma. The energy supply has the effect that these species emit radiation. Light is created having a spectrum with ratios in infrared, visible and/or ultraviolet range, the ratios comprising characteristic spectral lines for the respective species with regard to the position and intensity of the spectral lines.

This is used by the analysis device AE for tissue distinction, because if a plasma between electrode 10 and tissue 12 is ignited during surgical intervention, species of the tissue material are removed from tissue 12 and enter the plasma based on which the species contribute to the spectrum of the light of the intervention light appearance 13. For each new clinical indication the mostly different trace elements are decisive in order to be able to carry out a tissue distinction during surgery.

Thus, it is advantageous, if the composition of the test surface 26 or the counter electrode 25 is specifically selected based on the clinical indication for the intervention, particularly based on the expected composition of the tissue 12, that has to be treated in an RF surgical manner and/or the composition is specifically selected based on the emission spectrum during transition of material from counter electrode 25 in plasma phase. Substances, e.g. one or more metals (particularly pure metals or an alloy) or liquid (reference solution) containing selected species (reference substances) that are also present in a characteristic manner and/or are expected in the biological tissue 12 to be examined, can be selected as material for counter electrode 25 or test surface 26, for example Ca, K, Mg, Na, P, Cl, Cd, Zn, Rb, Cr, Co, Fe, I, Cu, Mn, Mo, Se, F, Si, As, Ni, Sn and V. In doing so, a test light appearance 44 can be created from which light features can be determined that can also be generated based on the intervention light appearance 13 created by the influence of instrument 11 on tissue 12. The test object 24 can be specifically selected by the surgery team based on the clinical indication.

Test object 24 can comprise two different test surfaces 26 that distinguish in their composition. For example, multiple metal plates with test surfaces 26 from different pure metals can be present. In doing so, the influence of the material of electrode 10 can be eliminated by calculation, because also the electrode material can contribute to the spectrum of the test light appearance 44 and/or the intervention light appearance 13.

Also electrode 10 can be specifically selected based on its composition for creation of the test light appearance 44, particularly based on the light features to be expected that contribute to the test light appearance 44 and/or the intervention light appearance 13 based on the material of electrode 10. The spectrum of the contributions of the material of electrode 10 to the test light appearance 44 and/or the light features thereof can be used as reference spectrum or reference light features, for example. This is particularly of importance, if electrode 10 is selected according to its material for the clinical indication with regard to the following surgery with system S. The spectral lines of the material of electrode 10 do preferably not superimpose the spectral lines of tissue 12 to be examined and/or spectral lines of material of counter electrode 25 in order to not distort test results and/or spectroscopy results gained based on the light of the test light appearance 44 or the intervention light appearance 13. The electrode material and the material of the test surface 26 and/or counter electrode 25 can be different in order to be able to carry out an unambiguous assignment of light features or signatures or trace elements.

The test of the operability of the analysis device AE can in addition or as an alternative to the above-described test for determination of the signal strength comprise a determination of the accuracy, e.g. the signal to noise ratio, over the entire spectrum of the test light appearance 44, over selected ranges of the spectrum and/or at one or more distinct spectral lines, indicating with which accuracy the signal intensity can be determined at one or more wavelengths due to the test light appearance 44. Preferably the accuracy is determined for one or more spectral lines that are present in the spectrum of the test light appearance 44 as well as in the spectrum of the intervention light appearance 13, because a possible method for tissue distinction applied by means of the analysis unit 23 is based on the determination of the signature of light features of the spectrum of the light of the intervention light appearance 13 and the determination of tissue features that have resulted in the signature based on the signature. For distinction between healthy tissue 12 and pathological tissue 12, for example, each signature can be calculated from intensity ratios of selected spectral lines that are characteristic for evaporated parts of the biological tissue 12. Based on the determined accuracy, it can be determined by the test device TE whether a tissue distinction is possible by means of the analysis device AE.

In addition or as an alternative, a distinction of one or more substances can be carried out for test purposes that are specifically used in one or more test surfaces 26. For example, the test device TE can be configured to determine signatures from light features of light of the test light appearance 44 calculated from intensities of multiple wavelengths or spectrum parts, wherein each signature is preferably calculated from intensity ratios of selected spectral lines characterizing material of the test surface 26 and/or electrode 10 and/or atmosphere between electrode 10 and test surface 26 transitioned into plasma condition. The test device TE can comprise means (not illustrated) for receiving information about the composition of the test surface 26 in order to submit such information to the test device TE. The test device TE can compare the distinction result based on the analysis of the light of the test light appearance with information that the test device TE has received via the means for receiving information about the composition of the test surface 26.

Based on the test result, the test device TE can output a signal about the test result to the user and/or identify one or more possible measures how the accuracy is to be increased or how a tissue distinction can be improved, for example by exchange or cleaning of one or more selected components of system S.

During determination of a ratio between intensities of spectral lines in the light of the test light appearance 44 and/or the intervention light appearance 13 the wavelength dependency of the transmissivity determined from the test light appearance 44 can be considered by means of a correction factor.

System S, particularly the analysis device AE, can be calibrated by means of the spectrum of the test light appearance 44 in order to be able to consider non-varying influence parameters on the transmission of light through the inlet of the optical fiber 14 up to the unit by means of which the light is converted in an electrical signal. In case of too high deviations of the light power in the positive or negative direction, this can be recognized by system S and can be compensated, e.g. by adaption of the integration time or by a correction factor of the analysis unit 23. A calibration of the entire system S with all relevant units that can influence the signal quality of a light spark can thus be determined and adapted. By means of the test device TE the system S can be calibrated. Calibration means that the accuracy of the system S is determined in the context of a test and that preferably based on the test with the test device TE at least one adjustment or a parameter of the system S, particularly the analysis device AE and/or the RF surgical apparatus E, is determined and adjusted in order to achieve a desired accuracy by means of the analysis device AE.

A test result that was determined from the light received from the test light appearance 44 can be gained prior to or during surgery and can be stored as reference for the remaining surgery application. By means of the reference, particularly a reference signal, for example, spectral lines in the light created by the intervention light appearance 13 between electrode 10 and tissue 12 can be identified.

Test device TE should advantageously be usable in the sterile area 29 such that a test of the transmission is possible, also after an application during surgery. The advantage for the user is the function test of system S prior or after an application directly at the operating table. The test device TE can be used for testing the signal quality of a light appearance, particularly a light spark for tissue distinction for a system and/or for testing the analysis device AE for optical emission spectroscopy. The test device TE can be used for testing the signal quality or the spark quality or the expected spark quality of a light spark or the analysis device AE prior to or after application of a tissue distinction.

Based on the test, the test device TE can automatically identify one or more adjustments for the test. For example, based on the evaluation of the test light appearance, it can be determined that the adjustment of the RF generator for creating the test light appearance 44 has to be adapted in order to create a test light appearance 44 based on which more accurate determination about the operability of the analysis device AE can be made and the test can be automatically repeated with the adapted adjustment. The voltage supplied by the RF generator 21 can be varied in order to avoid that the electrode 10 burns off during spark creation. In addition, the voltage supplied by the RF generator 21 is preferably variable such that the desired elements are excited and the spectral lines distinguish sufficiently from background noise.

Based on the test, the test device TE can automatically define one or more adjustments for the system S for the intervention or can determine and particularly limit adjustment possibilities. The one or more adjustments or adjustment possibilities are preferably gained based on the test result from the evaluation of the test light appearance 44. System S can be configured to define an adjustment or possible adjustments for the creation of the intervention light appearance 13, the capture of light of the intervention light appearance 13, the conversion of captured light of the intervention light appearance 13 in an electrical signal and/or the analysis of the signal based on the evaluation of the signal due to the light of the test light appearance 44. Based on the test result, the creation and/or analysis of the signal due to the light appearance 13 created by the electrosurgical intervention on the body of the patient, can be specifically influenced by the test device TE. In doing so, it can be ensured that intervention light appearances 13 are created based on the conditions during the intervention that allow an analysis result having a specific significance, particularly a specific accuracy.

According to an embodiment of the invention, a test device TE for testing, particularly calibrating of an analysis device AE for analysis of light appearances 13, 44 is provided that are created by an RF surgical instrument 11.

The test device TE comprises a test object 24 (in simple embodiments of the invention this can comprise that the test device is formed by the test object), wherein the test object is configured for creation of a plasma light appearance, the light of which can be captured by a light receiving unit 14. In embodiments the test object 24 is configured for creation of a plasma test light appearance 44 in that a plasma test light appearance 44 can be created between the test object 24 and instrument 11 by means of the instrument 11 that is arranged in an ignition distance or closer to the test object 24. The test object 24 is preferably configured and determined to be arranged and used during preparation and/or execution of a planned surgery. The test device TE is preferably a device of an RF surgical system S that comprises an RF surgical instrument 11 and an analysis device AE for analysis of light appearances 13, 44 created by the RF surgical instrument 11. The test object 24 serves preferably for execution of a function test and/or determination of a suitable adjustment—prior to and/or during a planned surgery—of the analysis device AE and/or other devices of the RF surgical system S by creation of a test light appearance 44 on or in the test object 24, preferably on a test surface 26 of the test object 24. In doing so, it can be tested whether the analysis device AE is operable during surgery and/or the operability of the analysis device AE can be improved in this way. In addition, a method 100 for testing, particularly calibrating, of an analysis device AE for analysis of light appearances 13, 44 is provided, wherein the light appearances 13, 44 are created by an RF surgical instrument 11. Method 100 comprises the creation of a test light appearance 44 between a test object 24 and an electrode 10. Light of the test light appearance 44 is received by a light receiving unit 14. Method 100 can preferably be carried out by a member of the surgery team, particularly the surgeon or a surgery assistant.

The invention claimed is:

1. A test device for calibrating an analysis device for analysis of light appearances created by an RF surgical instrument, the test device comprising a test object having an opening, the test device configured for creation of a plasma test light appearance, the plasma test light appearance having a light that may be received by a light receiving unit, wherein the test device is configured to determine a calibration of the analysis device from specific light features of the test light appearance.

2. The test device according to claim 1, wherein the test object is configured to define an orientation of the instrument, an adapter for the instrument, an electrode and/or a light receiving unit relative to the test surface, in that the test object is configured to guide the instrument and/or the light receiving unit during insertion of the instrument and/or the light receiving unit into the opening of the test object, such that the instrument and/or the light receiving unit automatically take a position such that the instrument and/or the light receiving unit have a defined orientation relative to the counter electrode.

3. A test device for calibrating an analysis device for analysis of light appearances created by an RF surgical instrument, the test device comprising a test object having an opening, the test device configured for creation of a plasma test light appearance, the plasma test light appearance having a light that may be received by a light receiving unit, wherein the test object is configured to define an orientation of the instrument, an adapter for the instrument, an electrode and/or a light receiving unit relative to a test surface, in that the test object is configured to guide the instrument and/or the light receiving unit during insertion of the instrument and/or the light receiving unit into the opening of the test object, such that the instrument and/or the light receiving unit automatically take a position such that the instrument and/or the light receiving unit have a defined orientation relative to a counter electrode.

4. The test device according to claim 3, wherein the test object comprises the test surface for creation of the test light appearance between an electrode, particularly an electrode of the instrument and the test surface.

5. The test device according to claim 3, wherein the test object can be arranged in a sterile operation area.

6. The test device according to claim 3 comprising an evaluation unit configured to (a) evaluate whether the analysis device is operable and/or (b) output a signal or a value to a user based on which the user can evaluate whether the analysis device is operable, based on light features of the received light of a test light appearance created by means of the test object.

7. The test device according to claim 3, wherein the test device is configured to determine a sensitivity of an analysis device at at least one wavelength and/or a transmissivity of the analysis device at at least one wavelength based on the test light appearance.

8. The test device according to claim 3, wherein the test device is configured to determine signatures from light features of the light of the test light appearance that are calculated from intensities of multiple wavelengths or spectrum parts, wherein each signature is preferably calculated from intensity ratios of selected spectral lines being characteristic of at least one of parts of a material of the test surface, parts of a material of the electrode, and an atmosphere between the electrode and the test surface being transitioned into a plasma condition.

9. The test device according to claim 3, wherein the test object comprises at least one substance selected based on its emission spectrum.

10. The test device according to claim 3, wherein the test object comprises at least two different test surfaces.

11. The test device according to claim 3, wherein the test object comprises specific substances that are also present or that are expected to be present in the tissue to be examined or to be treated in order to create a test light appearance from which light features can be determined that can also be determined from a light appearance created by the influence of the instrument on the tissue.

12. The test device according to claim 3, wherein the test device is configured to define a value or a value range based on the test light appearance due to the test with the test device for at least one parameter.

13. The test device according to claim 12, wherein the at least one parameter is at least one of a control parameter and/or an evaluation parameter.

14. The test device according to claim 3, wherein the test object is configured to define a minimum distance between the electrode and a test surface of the test object and/or wherein the test device is configured to define the atmosphere between an electrode and the test surface of a test object.

15. An RF surgical system, comprising:
the test device according to claim 3;
the analysis device;
the RF surgical instrument,
wherein the test device is configured to automatically determine an approach to or a position of the electrode near the test surface for creation of a test light appearance and based thereon to select or modify one or more adjustments and/or adjustment possibilities of the test device, the analysis device, and/or the RF surgical instrument.

16. A system comprising:
the test device according to claim 3; wherein the adapter is attached to
a light receiving unit and the adapter is releasable attached to the RF surgical instrument.

17. A method for calibrating an analysis device configured for analysis of light appearances created by the influence of an RF surgical instrument on biological tissue, the method comprising:
creating a test light appearance between a test object and an electrode;
receiving a light of the test light appearance by a light receiving unit; and
determining a calibration of the analysis device from specific light features of the test light appearance.

18. The method of claim 17, wherein the method is performed by a member of a surgery team.

19. The method of claim 18, wherein the method is performed by one of a surgeon or a surgery assistant.

20. An RF surgical system, comprising:
the test device according to claim 1;
the analysis device;
the RF surgical instrument,
wherein the test device is configured to automatically determine an approach to or a position of the electrode near the test surface for creation of a test light appearance and based thereon to select or modify one or more adjustments and/or adjustment possibilities of the test device, the analysis device, and/or the RF surgical instrument.

* * * * *